United States Patent
Durrant

(10) Patent No.: US 9,580,512 B2
(45) Date of Patent: Feb. 28, 2017

(54) CD55-INTERACTION PARTNERS AND THE USES THEREOF

(75) Inventor: Lindy Gillian Durrant, Nottingham (GB)

(73) Assignee: Cancer Research Technology Limited, London (GB)

(*) Notice: Subject to any disclaimer, the term of this patent is extended or adjusted under 35 U.S.C. 154(b) by 0 days.

(21) Appl. No.: 12/559,342

(22) Filed: Sep. 14, 2009

(65) Prior Publication Data

US 2010/0136013 A1 Jun. 3, 2010

Related U.S. Application Data

(62) Division of application No. 10/536,636, filed as application No. PCT/GB03/05163 on Nov. 26, 2003, now abandoned.

(30) Foreign Application Priority Data

Nov. 27, 2002 (GB) .................................. 0227644.2

(51) Int. Cl.
*A61K 39/395* (2006.01)
*C07K 16/28* (2006.01)
*C07K 16/30* (2006.01)
*A61K 39/00* (2006.01)

(52) U.S. Cl.
CPC .......... *C07K 16/2896* (2013.01); *C07K 16/30* (2013.01); *A61K 2039/505* (2013.01); *C07K 2319/30* (2013.01)

(58) Field of Classification Search
None
See application file for complete search history.

(56) References Cited

U.S. PATENT DOCUMENTS

| 4,916,213 A * | 4/1990 | Scannon et al. ............ 424/183.1 |
| 7,267,821 B2 | 9/2007 | Durrant et al. |
| 2003/0219434 A1* | 11/2003 | Carter et al. ............... 424/141.1 |

FOREIGN PATENT DOCUMENTS

| WO | WO 88/06452 | * | 7/1988 |
| WO | WO 98/06838 | | 2/1998 |
| WO | WO 9943800 | * | 9/1999 |
| WO | WO 00/37489 | | 6/2000 |

OTHER PUBLICATIONS

Price et al., Complement-Dependent Cytotoxicity of Anti-Human Osteogenic Sarcoma Monoclonal Antibodies. Br. J. Cancer (1982) 46: 610-10.*
Durrant et al. A Neoadjuvant Clinical Trial in Colorectal Cancer Patients of the Human Anti-Idiotypic Antibody 105AD7, Which Mimics CD55. Clinical Cancer Research vol. 6, 422-430, Feb. 2000.*
Maxwell-Armstrong et al. Randomized double-blind phase II survival study comparing immunization with the anti-idiotypic monoclonal antibody 105AD7 against placebo in advanced colorectal cancer. British Journal of Cancer, 2001, 84:1443-1446.*
Di Gaetano et al. Synergism between fludarabine and rituximab revealed in a follicular lymphoma cell line resistant to the cytotoxic activity of either drug alone. British Journal of Haematology (2001), 114(4), 800-809.*
Blok et al. A possible role of CD46 for the protection in vivo of human renal tumor cells from complement-mediated damage. Lab Invest 2000, 80:335-344.*
Gelderman et al. The inhibitory effect of CD46, CD55, and CD59 on complement activation after immunotherapeutic treatment of cervical carcinoma cells with monoclonal antibodies or bispecific monoclonal antibodies. Lab Invest. Apr. 2002;82(4):483-93.*
Durrant et al. Enhanced Cell-mediated Tumor Killing in Patients Immunized with Human Monoclonal Antiidiotypic Antibody 105AD7. Cancer Res 1994;54:4837-4840.*
Koprowski et al., Human anti-idiotype antibodies in cancer patients: Is the modulation of the immune response beneficial for the patient? Proc. natl. Acad. Sci. U.S.A. 81, 216, 1984.*
Maxwell-Armstrong et al, Randomized double-blind phase II survival study comparing immunization with the anti-idiotypic monoclonal antibody 105AD7 against placebo in advanced colorectal cancer. Br J Cancer. Jun. 2001; 84(11): 1443-1446. Abstract.*
Baldwin, et al., "Monoclonal Antibody 791T/36 for Tumor Detection and Therapy for Metastases," *Symposium on Fundamental Cancer Research*, 1983, pp. 437-455, vol. 36.
Bradley, R., et al., "A Monoclonal Antibody Directed Against SCR1-2 of Complement Control Protein, CD55 Enhances C3 Deposition and Tumour Cell Lysis," *British Journal of Cancer*, 2003, p. S39, vol. 88(1).
Durrant, L., et al., "Flow Cytometric Screening of Monoclonal Antibodies for Drug or Toxin Targeting to Human Cancer," *Journal of the National Cancer Institute*, 1989, pp. 688-696, vol. 81(9).
Golay, J., et al., "Biologic Response of B Lymphoma Cells to Anti-CD20 Monoclonal Antibody Rituximab in Vitro: CD55 and CD59 Regulate Complement-Mediated Cell Lysis," *Blood*, 2000, pp. 3900-3908, vol. 95(12).
Golay, J., et al., "CD20 Levels Determine the in Vitro Susceptibility to Rituximab and Complement of B-Cell Chronic Lymphocytic Leukemia; Further Regulation by CD55 and CD59," *Blood*, 2001, pp. 3383-3389, vol. 98(12).
Hamann, J., et al., "Characterization of the CD55 (DAF)-Binding Site on the Seven-Span Transmembrane Receptor CD97," *European Journal of Immunology*, 1998, pp. 1701-1707, vol. 28(5).
Pimm, M., et al., "A Bispecific Monoclonal Antibody Against Methotrexate and a Human Tumour Associated Antigen Augments Cytotoxicity of Methotrexate-Carrier Conjugate," *British Journal of Cancer*, 1990, pp. 508-513, vol. 61(4).
Spendlove, I., et al., "A Therapeutic Human Anti-Idiotypic Antibody Mimics CD55 in Three Distinct Regions," *Eur. J. Immunol.*, 2000, pp. 2944-2953, vol. 30(10).

(Continued)

*Primary Examiner* — Maher Haddad
(74) *Attorney, Agent, or Firm* — Alston & Bird LLP

(57) ABSTRACT

The invention relates to the use of a binding member that binds to both SCR1 and SCR2 of CD55 in the treatment of tumours and leukaemia. The binding member may be an antibody that binds to SCR1 and SCR2 of CD55 and neutralizing CD55 and making cancer cells susceptible to complement-mediated attack.

14 Claims, 2 Drawing Sheets

(56) References Cited

OTHER PUBLICATIONS

Figure 2:
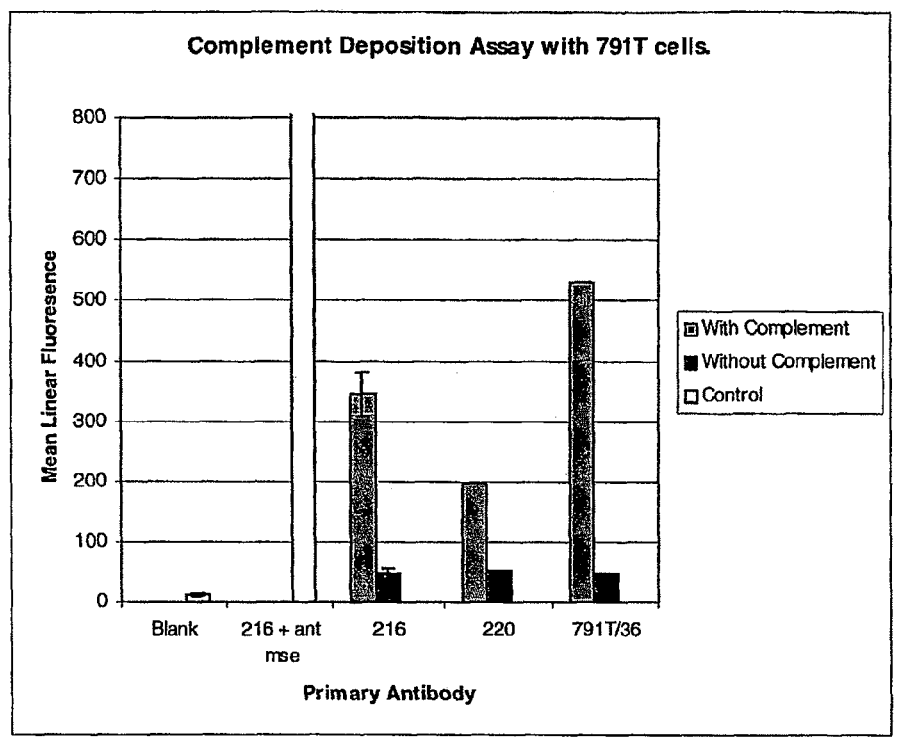

Spendlove, I., et al., "Decay Accelerating Factor (CD55): A Target for Cancer Vaccines?," *Cancer Research*, 1999, pp. 2282-2286, vol. 59(10).
Spendlove, I., et al., "Mapping the Binding Site of a Novel Antibody to SCR-1 and 2 of CD55," *Immunology*, 1999, p. 101, vol. 98(1).
Byers, V.S., et al., "Phase I Study of Monoclonal Antibody-Ricin A Chain Immunotoxin XomaZyme-791 in Patients with Metastatic Colon Cancer," *Cancer Research*, Nov. 1, 1989, pp. 6153-6160, vol. 49.
Farrands, P.A., et al., "Localisation of Human Osteosarcoma by Antitumour Monoclonal Antibody," *The Journal of Bone and Joint Surgery*, Nov. 1983, pp. 638-640, vol. 65-B(5).
"Rituximab Dosage," Drugs.com, http://www.drugs.com/dosage/rituximab.html (downloaded Oct. 30, 2015).
Armitage, N.C., et al., "The Localization of an Anti-tumor Monoclonal Antibody (791 T/36) in Gastrointestinal Tumors," *Br J. Surg.*, Jun. 1984, pp. 407-412, vol. 71, No. 6.
Farrands, P.A., et al., "Localisation of Human Osteosarcoma by Intitumour Monoclonal Antibody," *J. Bone Joint Surg.*, Nov. 1983, pp. 638-640, vol. 65-B, No. 5.
Farrands, P.A., et al., "Radioimmunodetection of Human Colorectal Cancers by an Anti-tumour Monoclonal Antibody," *Lancet*, Aug. 21, 1982, pp. 397-400.
E.B. Austin, et al., *Human Monoclonal Anti-Idiotypic Antibody to the Tumor-Associated Anti-Body 791T/36*, Immunology, 67 (1989) 525-530.

\* cited by examiner

Figure1a. CDR amino acid sequences of 105AD7 anti-idiotypic antibody

| CDR | Kappa (L) | Heavy (H) |
|---|---|---|
| 1 | itcRASQDISSFLNwyq | ntSGVCVGwi |
| 2 | liyAASILQSgvp | wlaHIYWDDDKRYSPSLKSrlt |
| 3 | yycQQSYKTPPSfgq | caqVLYYDFWSGYLEYFAYwgq |

Figure1b. Alignment of CDRs with CD55

```
            SCR-1 (1C)           -->|<--            SCR-2 (2N)
83                    93                  101                         112
K G S Q W S D I E E F    C N R S   C E V  P  T R L N S A  S L K Q P
  •   • •     • •   •              •   •   |      •   |  • • •
R A S Q - - D I S S F    L N         W D D    K R Y S P  S L K S

105AD7 CDR L1                            105AD7 CDR H2
```

```
                    SCR-2 (2C)
              145                   157          aa number
S L S P K L T  C L Q N L K W S T A V E  F C K K  CD55
               •   • •     | • |
             V L Y Y D F W S G Y L E Y
                    105AD7 H3
```

CD55-INTERACTION PARTNERS AND THE USES THEREOF

CROSS-REFERENCE TO RELATED APPLICATIONS

This application is a divisional patent application of U.S. application Ser. No. 10/536,636, filed Aug. 22, 2005, now abandoned, which claims the benefit of International Patent Application No. PCT/GB03/05163, filed Nov. 26, 2003, which claims priority to Great Britain Application No. 0227644.2, filed Nov. 27, 2002, all of which are herein incorporated by reference in their entirety.

The present invention relates to specific binding members and their use in therapy. In particular, the invention relates to specific binding members which bind to CD55, their use in the modulation of complement activation and the treatment of disease, for example, neoplastic disease.

The human complement system consists of a highly efficient recognition and effector mechanism that consists of 30 serum or cellular components including activated proteins, receptors and positive and negative regulators. In brief, the complement cascade consists of a triggering step, an amplification step with a feedback loop and finally, a membrane attack or lytic step. The central component of the complement system is C3. Generation of C3b by the classical or alternative pathway is crucial for opsonisation and lysis. The classical pathway is initiated when component C1 via its Clq subcomponent attaches to an antibody to form an immune complex. For the alternative pathway, however, there is no initiating factor equivalent to antibody. Rather it is in a state of continuous, low level activation as a result of spontaneous hydrolysis of a thioester group in native C3. This results in binding of C3 to non-specific acceptor molecules in plasma or on cell surfaces. This can result in the formation of C3 convertases and creation of a feedback loop. Because of its potent pro-flammatory and destructive capabilities, there is a regulatory system designed to prevent complement activation both in the fluid phase and on bystander tissues.

There are four membrane bound complement regulatory proteins namely complement receptor 1 (CR1), CD55, CD46 and CD59 (Liszewski et al 1996. Adv Immunol 61:201-283). Regulation is either accomplished by:
1. Spontaneous decay of activated proteins and enzyme complex (i.e. short half life)
2. Destabilisation and inhibition of activation complexes
3. Proteolytic cleavage of "activated" components.

CD46, CD55 and CD59 are widely expressed on many tissues, including surface epithelia and tumour tissues. In contrast, CR1 expression is limited to peripheral blood cells and is therefore not directly involved in protection of solid tumours.

Most tumours are of epithelial origin and, although most surface epithelia express complement regulatory proteins, tumours show variable expression of CD55, CD46 and CD59. The majority of colorectal and thyroid cancers express high levels of all three complement regulatory proteins (Niehans et al., 1996 Am J Pathol 149:129-142; Li et al., 2001 Br. J. Cancer 84:80-86; Thorsteinsson, 1998 APMIS 106:869-878; Yamakawa et al., 1994 Cancer 73:2808-2817). Ductal carcinoma of the breast shows the most variation in phenotype with some tumours expressing only one inhibitor while others express different combinations of two or three inhibitors (Niehans et al., 1996 supra; Thorsteinsson et al., 1998 supra). Renal cell carcinoma has weak to moderate expression of one to three inhibitors, generally CD55 and CD59 (Niehans et al., 1996 supra) whereas non-small cell lung carcinomas and ovarian and cervical cancers usually express CD59 and CD46 with variable CD55 immunoreactivity (Niehans et al., 1996 supra; Bjorge et al., 1977 Cancer Immunol Immunother 42:185-192; Simpson et al., 1997 Am J Pathol 151:1455-1467). Similar results have been obtained with established cell lines (Bjorge et al., 1996. supra; Gorter et al 1986 Lab Invest 74 1; Juhl et al., 1997 J. Surgical Oncol. 64:222-230; Li at al., 2001 supra).

All three complement regulatory proteins are expressed on vascular endothelium. Their specific roles during inflammation when the risk of complement mediate injury may be increased remains to be determined. CD55, but not CD46 or CD59, is up-regulated on endothelial cells by the pro-inflammatory mediators TNFα, IL-1β, and IFN-γ, and also by the MAC (membrane attack complex) and thrombin. These results suggest that CD55 is of critical importance in protecting endothelial cells from complement during inflammation and coagulation. Furthermore it has recently been shown that retraction of endothelial cells exposing sub-endothelial extracellular matrix is a potent inducer of the alternative complement pathway releasing anaphylatoxins that stimulate inflammation. As tumours frequently have disregulated endothelium, with exposed vessel walls, the tumour environment may induce complement activation. This may be one of the reasons that tumour cells over-express complement regulatory receptors. However, it has been shown that both tumour cells and endothelial cells can actually secrete CD55 but not CD46 into their extracellular matrix (ECM) (Hindmarsh and Marks, 1998 J. Immunol. 160:6128-6136). Hindmarsh and Marks showed that tumour but not endothelial derived CD55 is functionally active and can prevent deposition of C3b. However, deposition of matrix CD55 could not be up-regulated by inflammatory cytokines. More recently the present inventors have shown that both CD55 and CD59 can be deposited into extracellular matrix by both tumours and endothelial cells and the latter can be considerably up-regulated by the potent angiogenesis growth factor VEGF (Li et al., 2001 supra). Furthermore, CD55 deposited by endothelial cells stimulated with VEGF was shown to be functionally active. VEGF is unusual, as it is the only cytokine identified to date that up-regulates both cell surface expression and deposition of CD55 into the ECM.

As most tumours secrete high levels of VEGF to induce angiogenesis they will stimulate expression of CD55 on endothelial cells and within ECM. Interestingly immunohistochemistry of colorectal tumours with anti-CD55 monoclonal antibodies shows intense staining of tumour stroma (Li et al., 2001 supra; Simpson et al., 1997 supra; Niehans et al., 1996 supra) and blood vessels (Niehans et al., 1996 supra). CD55 deposited within ECM is covalently bound as it cannot be released by strong acids or alkalis.

CD55 binds C3 convertases from both the classical and alternative complement pathways displacing C2b and C3b respectively. It can, therefore, prevent C3b deposition and inhibit the downstream assembly of the membrane attack complex. CD55 has an extracellular domain that is composed of 4 contiguous short consensus (SCR) domains and a threonine/serine rich region proximal to the cell surface. It has a single N-glycosylation site between the first and second SCR domains and is heavily O-glycosylated in the threonine and serine rich regions. It is attached to the cell membrane by a glycophosphoinositol (GPI) anchor and is expressed by all cells exposed to complement, namely, red blood cells, leukocytes, endothelial and epithelial cells.

CD55 has also been detected in low amounts in plasma, saliva and urine. The biological significance of this soluble form remains unclear as it has never been shown to be functionally active. Recently it has been shown that HeLa cells and HUVEC incorporate CD55 into their extracellular matrix and that this covalently linked CD55 can inhibit C3b deposition and the release of the pro-inflammatory anaphylatoxin C3a (Hindmarsh and Marks, 1998 supra).

As well as making tumour cells susceptible to in situ complement activation, antibodies inhibiting the functions of complement regulatory proteins may also make tumour cells susceptible to monoclonal antibody mediated complement dependent cellular cytotoxicity. A chimeric anti-LewisY monoclonal antibody (cH18A) mediated modest complement mediated cell lysis of two lung adenocarcinomas cell lines. However addition of antibodies that block the function of CD46, CD55 and CD59 considerably enhance complement mediated lysis. Use of multiple blocking antibodies to the complement regulatory proteins produced more enhancement of cH18A mediated lysis than any single antibody (Azuma et al., 1995. Scand J Immunol 42:202-208). Several groups have generated bispecific antibodies with one arm targeting a tumour cell surface antigen and the other targeting the functional domain of a complement regulatory protein. A bispecific antibody targeting HLA and SCR3 of CD55 resulted in a 92% enhancement of C3b deposition on renal tumours. Similarly in the same study a bispecific antibody targeting a renal tumour antigen and the SCR3 of CD55 resulted in a 25-400% increase in C3b deposition on renal tumours and rendered the cells susceptible to complement mediated lysis (Blok et al., 1998 J Immunol 160:3437-3443). Finally when a chimeric anti-CD37 monoclonal antibody was used to activate the classical complement pathway, a bispecific Fab'gamma construct targeting a lymphoma specific antigen and the CD59 functional domain increased cell lysis by 3-5 fold (Harris et al., 1997 Clin. Exp. Immunol. 107:364-371).

However, although previous studies have shown that monoclonal antibodies recognising SCR3 of CD55 could partially neutralise CD55 leading to enhanced C3b deposition and assembly of the MAC complex, each of these antibodies merely compete for binding to SCR3 with the C3 convertases and therefore only partially neutralise CD55. Molecular constructs of CD55 have shown that SCR3 is the active domain of CD55 and that SCR2 and SCR4 are necessary to provide the correct conformation for C3 binding. No role for SCR1 in complement decay has been shown. However, although SCR2 is necessary to provide the correct conformation for C3 binding, studies with monoclonal antibodies to single SCR domains of CD55 have shown that only monoclonal antibodies that bind to SCR3 and not antibodies that bind to either SCR1 or SCR2 can neutralise CD55 (Coyne et al, 1992 J Immunol 149, 2906).

Imaging studies with the monoclonal antibody 791T/36 (Embleton et al 1981 Br. J. Cancer 43:582-587) in osteosarcomas, ovarian and colorectal tumours successfully imaged lesions as small as 1 cm³ (Farrands et al 1982 Lancet 2:397-400; Farrands et al 1983. J. of Bone and Joint Surg. 65:638-640; Armitage et al., 1985. Nucl Med Commun 6:623-631). Furthermore autoradiography of the resected tumours showed both cell surface and intense stromal localisation of the antibody (Armitage et al., 1984 Br J Surg 71:407-412). These studies illustrate that an anti-CD55 antibody can effectively localise in tumours without showing any normal tissue toxicity. In particular no detectable binding of radiolabeled antibody to blood cells and only background levels of radiolabel were seen on endothelium or normal tissues. The antigen recognised by 791T/36 was recently identified as CD55 (Spendlove et al Eur J. Immunol. 30:2944-2953; Spendlove et al Cancer Res. 59:2282-2286). Using CD55/CD46 chimeric constructs it was possible to map the binding site of 791T/36 to the first two SCR domains of CD55 with peptide analysis showing that 791T/36 can bind to three distinct regions of SCR1-2 of CD55. One region is in SCR1 and two are in SCR2.

WO00/5204 discloses a method for making antibodies, for example antibodies directed against decay accelerating factor (DAF, using a naïve antibody phage library. Although the document refers to the use of such antibodies in cancer diagnosis or therapy, no examples are provided other than a speculative example, in which antibody LU30 is suggested for use in assessing overexpression of DAF and for treatment of lung cancer particularly when combined with cytotoxic agents.

WO/04415 describes the production of the anti-idiotype antibody 105AD7 which was raised against antibody 791T/36 and speculates on potential therapeutic uses of the 105AD7 antibody.

However, to date, no therapeutically useful anti-CD55 antibodies other than anti SCR3 antibodies have been demonstrated. Therapeutic studies with antibodies directed to other SCRs of this molecule have been limited to immunoconjugated molecules. (See for example U.S. Pat. No. 4,916,213 (Xoma Corporation), U.S. Pat. No. 4,925,922 (Xoma Corporation) and Byers et al. 1987 Cancer Res 47:5042-5046). For example, Byers et al describes studies with 791T/36 linked to ricin A chain, showed significantly inhibition of tumour growth in athymic mice. 791T/36-RTA was therefore screened in a phase I clinical trial in advanced colorectal cancer patients (Byers et al 1989. Cancer Research 49:6153-6160). However the trial was unsuccessful due to dose limiting toxicity.

Surprisingly, the present inventors have now demonstrated that, although previous studies have demonstrated that antibodies which target either SCR 1 or SCR 2 of CD55 failed to have any neutralisation effect on CD55, an antibody which targets both SCR 1 and SCR2 not only effectively neutralises CD55 but is superior to a SCR3 neutralising antibody.

Accordingly, in a first aspect, the present invention provides a method of neutralisation of CD55, comprising administration of a naked binding member which specifically binds to SCR1 and SCR2 of CD55.

By neutralising CD55, enhanced complement deposition may be facilitated. Accordingly, in a second aspect, the invention provides a method of enhancing complement deposition on a tissue comprising administration of a naked binding member which specifically binds to SCR1 and SCR2 of CD55.

The methods of the invention may be used in vitro or in vivo.

As described above, CD55 is commonly found on many tumour cell surfaces, where it serves to inhibit complement deposition. By neutralising such molecules on tumour cells, the methods of the invention enable complement mediated attack of tumour cells. Accordingly, in a further aspect of the present invention, there is provided a method of treating cancer comprising administration of a therapeutically effective amount of a naked binding member which specifically binds to SCR1 and SCR2 of CD55 to a mammal in need thereof.

In a further aspect, there is provided the use of (i) a naked binding member which binds to both SCR1 and SCR2 of CD55 or (ii) a nucleic acid encoding said binding member in the preparation of a medicament for the neutralisation of CD55.

In a further aspect, there is provided a naked binding member which binds to both SCR1 and SCR2 for use in the treatment of cancer.

In a further aspect, there is provided the use of (i) a naked binding member which binds to both SCR1 and SCR2 of CD55 or (ii) a nucleic acid encoding said binding member in the preparation of a medicament for treating cancer.

The present invention also provides a pharmaceutical composition for the treatment of cancer, wherein the composition comprises a naked binding member that binds to both SCR1 and SCR2 of CD55.

Specific Binding Member

As used herein, a "binding member" is a member of a pair of molecules which have binding specificity for one another. The binding member is, therefore, a specific binding member. The members of a binding pair may be naturally derived or wholly or partially synthetically produced. One member of the pair of molecules may have an area on its surface, which may be a protrusion or a cavity, which specifically binds to and is therefore complementary to a particular spatial and polar organisation of the other member of the pair of molecules. Thus, the members of the pair have the property of binding specifically to each other. Examples of types of binding pairs are antigen-antibody, biotin-avidin, hormone-hormone receptor, receptor-ligand, enzyme-substrate. The present invention is concerned with antigen-antibody type reactions, although a binding member of the invention and for use in the invention may be any moiety which can bind to both SCR1 and SCR2 of CD55.

As used herein, "naked" means that the binding member of or for use in the present invention is not bound to, for example conjugated with, any agent, for example ricin, having anti-tumour properties.

Antibodies

An "antibody" is an immunoglobulin, whether natural or partly or wholly synthetically produced. The term also covers any polypeptide, protein or peptide having a binding domain which is, or is homologous to, an antibody binding domain. These can be derived from natural sources, or they may be partly or wholly synthetically produced. Examples of antibodies are the immunoglobulin isotypes and their isotypic subclasses and fragments which comprise an antigen binding domain such as Fab, scFv, Fv, dAb, Fd; and diabodies.

The binding member of the invention may be an antibody such as a monoclonal or polyclonal antibody, or a fragment thereof. The constant region of the antibody may be of any class including, but not limited to, human classes IgG, IgA, IgM, IgD and IgE. The antibody may belong to any sub class e.g. IgG1, IgG2, IgG3 and IgG4. IgG1 is preferred. In preferred embodiments the antibody is 791T/36 produced by the cell line deposited with ATCC under accession no. HB9173.

As antibodies can be modified in a number of ways, the term "antibody" should be construed as covering any binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

It has been shown that fragments of a whole antibody can perform the function of binding antigens. Examples of such binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341:544-546 (1989)) which consists of a VH domain; (v) isolated CDR regions; (vi) F(ab')$_2$ fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., *Science* 242:423-426 (1988); Huston et al., *PNAS USA* 85:5879-5883 (1988)); (viii) bispecific single chain Fv dimers (PCT/US92/09965) and (ix) "diabodies", multivalent or multispecific fragments constructed by gene fusion (WO94/13804; P. Hollinger et al., *Proc. Natl. Acad. Sci. USA* 90:6444-6448 (1993)).

A fragment of an antibody or of a polypeptide for use in the present invention, for example, a fragment of the 791T/36 antibody, generally means a stretch of amino acid residues of at least 5 to 7 contiguous amino acids, often at least about 7 to 9 contiguous amino acids, typically at least about 9 to 13 contiguous amino acids, more preferably at least about 20 to 30 or more contiguous amino acids and most preferably at least about 30 to 40 or more consecutive amino acids. A preferred group of fragments are those which include all or part of the CDR regions of monoclonal antibody 791T/36. A preferred group of fragments are those which include all or part of the CDR regions of monoclonal antibody 791T/36.

A "derivative" of such an antibody or polypeptide, or of a fragment of a 791T/36 antibody means an antibody or polypeptide modified by varying the amino acid sequence of the protein, e.g. by manipulation of the nucleic acid encoding the protein or by altering the protein itself. Such derivatives of the natural amino acid sequence may involve insertion, addition, deletion and/or substitution of one or more amino acids, preferably while providing a peptide having anti-CD55 activity, for example, CD55 neutralisation activity. Preferably such derivatives involve the insertion, addition, deletion and/or substitution of 25 or fewer amino acids, more preferably of 15 or fewer, even more preferably of 10 or fewer, more preferably still of 4 or fewer and most preferably of 1 or 2 amino acids only.

The term "antibody" includes antibodies which have been "humanised". Methods for making humanised antibodies are known in the art. Methods are described, for example, in Winter, U.S. Pat. No. 5,225,539. A humanised antibody may be a modified antibody having the hypervariable region of a monoclonal antibody such as 791T/36 and the constant region of a human antibody. Thus the binding member may comprise a human constant region.

The variable region other than the hypervariable region may also be derived from the variable region of a human antibody and/or may also be derived from a monoclonal antibody such as 791T/36. In such case, the entire variable region may be derived from murine monoclonal antibody 791T/36 and the antibody is said to be chimerised. Methods for making chimerised antibodies are known in the art. Such methods include, for example, those described in U.S. patents by Boss (Celltech) and by Cabilly (Genentech). See U.S. Pat. Nos. 4,816,397 and 4,816,567, respectively.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementary determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

In preferred embodiments of the invention, the binding member binds to CD55 SCR1 (amino acids 83-93) and SCR2 (amino acids 101-112 and amino acids 145-157) of the sequences shown in FIG. 1b.

The binding member may comprise one or more of the CDRs of the antibody, or a fragment thereof, produced by the cell line deposited at ATCC under accession number HB9173.

As described above, in a preferred embodiment of the invention, the binding member is the antibody 791T/36 produced by the hybridoma cell deposited under ATCC accession number HB9173. As used herein, reference to "791T/36" includes sequences which show substantial homology with 791T/36. Preferably the degree of homology between 791T/36 complementary determining regions (CDRs) and the CDRs of other antibodies will be at least 60%, more preferably 70%, further preferably 80%, even more preferably 90% or most preferably 95%.

The percent identity of two amino acid sequences or of two nucleic acid sequences may be determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions ×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The NBLAST and XBLAST programs of Altschul, et al. (1990) J. Mol. Biol. 215:403-410 have incorporated such an algorithm. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilised as described in Altschul et al., (1997) Nucleic Acids Res. 25:3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., XBLAST and NBLAST) can be used. See http://www.ncbi.nlm.nih.gov.

Another example of a mathematical algorithm utilised for the comparison of sequences is the algorithm of Myers & Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis & Robotti (1994) Comput. Appl. Biosci., 10:3-5; and FASTA described in Pearson & Lipman (1988) Proc. Natl. Acad. Sci. 85:2444-8. Within FASTA, ktup is a control option that sets the sensitivity and speed of the search.

Where high degrees of sequence identity are present there will be relatively few differences in amino acid sequence. Thus for example they may be less than 20, less than 10, or even less than 5 differences.

The present inventors have shown that antibodies directed to SCR1 and SCR2 of CD55, for example 791T/36 antibodies and fragments and derivatives thereof can be used as cancer therapeutics to inactivate CD55 and make tumour cells susceptible to complement mediated attack. This is exemplified by localisation of the antibody within tumours of cancer patients and their subsequent enhanced survival (see the Examples). Accordingly the invention further provides the use of naked "fragments" or "derivatives" of 791T/36 or other polypeptides of the "791T/36" family which bind to both SCR1 and SCR2 CD55 epitopes in the preparation of an agent for treating cancer.

The binding members may be administered alone or in combination with one or more further agents. Thus, the present invention further provides products comprising a naked binding member, which binds to both SCR1 and SCR2 of CD55, and an active agent as a combined preparation for simultaneous, separate or sequential use in the treatment of cancer. Active agents may include chemotherapeutic agents including, Doxorubicin, taxol, 5-Fluorouracil (5 FU), Leucovorin, Irinotecan, Mitomycin C, Oxaliplatin, Raltitrexed, Tamoxifen and Cisplatin which may operate synergistically with the binding member of the present invention. Other active agents may include suitable doses of pain relief drugs such as non-steroidal anti-inflammatory drugs (e.g. aspirin, paracetamol, ibuprofen or ketoprofen) or opiates such as morphine, or anti-emetics. In further embodiments, the active agent may be a further binding member. Thus, in preferred embodiments the binding member may be administered in combination with one or more further binding members. Such binding members may include but are not limited to an anti-CD20 antibody e.g Rituxan (Rituximab)(Biogen IDEC (Cambridge, Mass., USA); an anti-VEGF antibody e.g. Avastin(bevacizumab), Genentech (South San Francisco, Calif., USA)/Roche (Basel, Switzerland); an anti-CD171A antibody, e.g. Panorex (edrecolomab) Centocor (Malvern, Pa., USA)/Glaxo Smith-Kline (Uxbridge, UK); an anti-CEA anti-idiotypic mAb e.g. CeaVac, Titan Pharmaceuticals (South San Francisco, Calif., USA); an anti-EGFR antibody e.g. Erbitux(cetuximab), ImClone(New York, USA)/Bristol Myers Squibb (New York, USA), Merck (Whitehouse Station, N.J., USA); an anti-HMFG anti-idiotypic mAb e.g TriAb, Titan Pharmaceuticals (South San Francisco, Calif., USA), an anti-EGFR antibody e.g. ABX-EGF, Abgenix (Fremont, Calif., USA)/Amgen Thousand Oaks, Calif.) and/or an anti-HER2 antibody e.g. Herceptin, Genentech (South San Francisco, Calif., USA).

Preferably, the active agent synergises with the binding member. The ability of the binding member to synergise with an active agent to enhance tumour killing may not be due to immune effector mechanisms but rather may be a direct consequence of inactivating CD55 allowing enhanced complement deposition and complement lysis. The binding member of the invention may carry a detectable label.

Treatment

"Treatment" includes any regime that can benefit a human or non-human animal. The treatment may be in respect of an existing condition or may be prophylactic (preventative treatment). Treatment may include curative, alleviation or prophylactic effects.

"Treatment of cancer" includes treatment of conditions caused by cancerous growth and includes the treatment of neoplastic growths or tumours.

Examples of tumours that can be treated by the system of the invention are, for instance, sarcomas, including osteogenic and soft tissue sarcomas, carcinomas, e.g., breast-, lung-, bladder-, thyroid-, prostate-, colon-, rectum-, pancreas-, stomach-, liver-, uterine-, cervical and ovarian carcinoma, lymphomas, including Hodgkin and non-Hodgkin lymphomas, neuroblastoma, melanoma, myeloma, Wilms tumor, and leukemias, including acute lymphoblastic leukaemia and acute myeloblastic leukaemia, gliomas and retinoblastomas.

The binding member may, upon binding to SCR1 and SCR2 of CD55 present on cancerous cells or tissues, including tumour and non-tumour cells, neutralise CD55 and enhance complement deposition and complement mediated lysis of these cells.

The compositions and methods of the invention may be particularly useful in the treatment of existing cancer and in the prevention of the recurrence of cancer after initial treatment or surgery.

Administration

Binding members of the present invention may be administered alone but will preferably be administered as a pharmaceutical composition, which will generally comprise a suitable pharmaceutical excipient, diluent or carrier selected dependent on the intended route of administration.

Binding members of the present invention may be administered to a patient in need of treatment via any suitable route. The precise dose will depend upon a number of factors, including the precise nature of the member (e.g. whole antibody, fragment or diabody), and the nature of the detectable label attached to the member.

Some suitable routes of administration include (but are not limited to) oral, rectal, nasal, topical (including buccal and sublingual), vaginal or parenteral (including subcutaneous, intramuscular, intravenous, intradermal, intrathecal and epidural) administration. Intravenous administration is preferred.

It is envisaged that injections (intravenous) will be the primary route for therapeutic administration of the compositions although delivery through a catheter or other surgical tubing is also envisaged. Liquid formulations may be utilised after reconstitution from powder formulations.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The composition may also be administered via microspheres, liposomes, other microparticulate delivery systems or sustained release formulations placed in certain tissues including blood. Suitable examples of sustained release carriers include semipermeable polymer matrices in the form of shared articles, e.g. suppositories or microcapsules. Implantable or microcapsular sustained release matrices include polylactides (U.S. Pat. No. 3,773, 919; EP-A-0058481) copolymers of L-glutamic acid and gamma ethyl-L-glutamate (Sidman et al, Biopolymers 22(1): 547-556, 1985), poly (2-hydroxyethyl-methacrylate) or ethylene vinyl acetate (Langer et al, J. Biomed. Mater. Res. 15: 167-277, 1981, and Langer, Chem. Tech. 12:98-105, 1982). Liposomes containing the polypeptides are prepared by well-known methods: DE 3,218, 121A; Epstein et al, PNAS USA, 82: 3688-3692, 1985; Hwang et al, PNAS USA, 77: 4030-4034, 1980; EP-A-0052522; E-A-0036676; EP-A-0088046; EP-A-0143949; EP-A-0142541; JP-A-83-11808; U.S. Pat. Nos. 4,485,045 and 4,544,545. Ordinarily, the liposomes are of the small (about 200-800 Angstroms) unilamellar type in which the lipid content is greater than about 30 mol. % cholesterol, the selected proportion being adjusted for the optimal rate of the polypeptide leakage.

Examples of the techniques and protocols mentioned above and other techniques and protocols which may be used in accordance with the invention can be found in Remington's Pharmaceutical Sciences, 16$^{th}$ edition, Oslo, A. (ed), 1980.

The composition may be administered in a localised manner to a tumour site or other desired site or may be delivered in a manner in which it targets tumour or other cells. Targeting therapies may be used to deliver the active agent more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

Pharmaceutical Compositions

As described above, the present invention extends to a pharmaceutical composition for the treatment of cancer, the composition comprising a naked binding member which binds to both SCR1 and SCR2 of CD55. Pharmaceutical compositions according to the present invention, and for use in accordance with the present invention may comprise, in addition to active ingredient, a pharmaceutically acceptable excipient, carrier, buffer stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

The formulation may be a liquid, for example, a physiologic salt solution containing non-phosphate buffer at pH 6.8-7.6, or a lyophilised powder.

Dose

The compositions are preferably administered to an individual in a "therapeutically effective amount", this being sufficient to show benefit to the individual. The actual amount administered, and rate and time-course of administration, will depend on the nature and severity of what is being treated. Prescription of treatment, e.g. decisions on dosage etc, is ultimately within the responsibility and at the discretion of general practitioners and other medical doctors, and typically takes account of the disorder to be treated, the condition of the individual patient, the site of delivery, the method of administration and other factors known to practitioners.

The optimal dose can be determined by physicians based on a number of parameters including, for example, age, sex, weight, severity of the condition being treated, the active ingredient being administered and the route of administration. In general, a serum concentration of polypeptides and antibodies that permits saturation of receptors is desirable. A concentration in excess of approximately 0.1 nM is normally sufficient. For example, a dose of 100 mg/m$^2$ of antibody provides a serum concentration of approximately 20 nM for approximately eight days.

As a rough guideline, doses of antibodies may be given weekly in amounts of 10-300 mg/m$^2$. Equivalent doses of antibody fragments should be used at more frequent intervals in order to maintain a serum level in excess of the concentration that permits saturation of CD55.

Production of Binding Members

The binding members of and for use in the present invention may be generated wholly or partly by chemical synthesis. The binding members can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2$^{nd}$ edition, Pierce Chemical Company, Rockford, Ill. (1984), in M. Bodanzsky and A. Bodanzsky, The Practice of Peptide Synthesis, Springer Verlag, New York (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Another convenient way of producing a binding member suitable for use in the present invention is to express nucleic acid encoding it, by use of nucleic acid in an expression system. Thus the present invention further provides the use of an isolated nucleic acid encoding a naked binding member which binds to both SCR1 and SCR2 of CD55 in the preparation of an agent for treating cancer.

Nucleic acid for use in accordance with the present invention may comprise DNA or RNA and may be wholly or partially synthetic. In a preferred aspect, nucleic acid for use in the invention codes for a binding member of the invention as defined above. The skilled person will be able to determine substitutions, deletions and/or additions to such nucleic acids which will still provide a binding member of the present invention.

Nucleic acid sequences encoding a binding member for use with the present invention can be readily prepared by the skilled person using the information and references contained herein and techniques known in the art (for example, see Sambrook, Fritsch and Maniatis, "Molecular Cloning", A Laboratory Manual, Cold Spring Harbor Laboratory Press, 1989, and Ausubel et al, Short Protocols in Molecular Biology, John Wiley and Sons, 1992), given the nucleic acid sequences and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding antibody fragments may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the sequences can be made, e.g. using site directed mutagenesis, to lead to the expression of modified peptide or to take account of codon preferences in the host cells used to express the nucleic acid.

The nucleic acid may be comprised as constructs in the form of a plasmid, vector, transcription or expression cassette which comprises at least one nucleic acid as described above. The construct may be comprised within a recombinant host cell which comprises one or more constructs as above. Expression may conveniently be achieved by culturing under appropriate conditions recombinant host cells containing the nucleic acid. Following production by expression a specific binding member may be isolated and/or purified using any suitable technique, then used as appropriate.

Binding members-encoding nucleic acid molecules and vectors for use in accordance with the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is *E. coli*.

The expression of antibodies and antibody fragments in prokaryotic cells such as *E. coli* is well established in the art. For a review, see for example Plückthun, *Bio/Technology* 9:545-551 (1991). Expression in eukaryotic cells in culture is also available to those skilled in the art as an option for production of a binding member, see for recent review, for example Reff, *Curr. Opinion Biotech.* 4:573-576 (1993); Trill et al., *Curr. Opinion Biotech.* 6:553-560 (1995).

Alternatively, the specific binding members for use B in the invention may be produced in transgenic organisms, for example mammals, avians, fish, insects or plants using methods known in the art. In such transgenic methods, nucleic acid encoding the binding member(s) may be introduced to the cell or embryo by methods including but not limited to direct injection, electroporation, nuclear transfer techniques or by use of vectors, e.g. viral vectors. In one preferred embodiment, the specific binding members are produced in avian tissues, preferably avian eggs, using, for example, the method as disclosed in GB 0227645.9, filed 27 Nov. 2002 and the subsequent PCT application claiming priority therefrom.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, Sambrook et al., *Molecular Cloning: A*

*Laboratory Manual:* 2$^{nd}$ Edition, Cold Spring Harbor Laboratory Press (1989). Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. eds., *Short Protocols in Molecular Biology*, 2$^{nd}$ Edition, John Wiley & Sons (1992).

The nucleic acid may be introduced into a host cell by any suitable means. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells under conditions for expression of the gene.

The nucleic acid may be integrated into the genome (e.g. chromosome) of the host cell. Integration may be promoted by inclusion of sequences which promote recombination with the genome in accordance with standard techniques. The nucleic acid may be on an extra-chromosomal vector within the cell, or otherwise identifiably heterologous or foreign to the cell.

Assays

The invention further provides assays for identification of further agents, for example antibodies that can be used for the enhancement of complement deposition on a cell sample or tissue and which can optionally be used in the treatment of cancer.

In a preferred aspect, the assay comprises an assay method for identification of an agent capable of inhibiting CD55 comprising steps:

a) bringing into contact a candidate agent with at least a portion of SCR1 and SCR2 of CD55; and
b) determining binding of said candidate agent to both SCR1 and SCR2.

In a further embodiment, the assay method comprises a method for identification of an agent capable of inhibiting CD55 comprising:

(a) bringing into contact a candidate agent with at least a portion of SCR1 and SCR2 of CD55 in the presence of a naked binding member which in the absence of the candidate agent is capable of binding both SCR1 and SCR2 of CD55; and
(b) determining the extent to which the candidate agent inhibits binding of the naked binding member to SCR1 and SCR2 of CD55.

The assays may further comprise the step of selecting a candidate agent which binds both SCR1 and SCR2 of CD55; and/or the step of determining the amount of complement deposition on a cell sample in the presence and absence of the candidate agent.

In preferred embodiments of the assays of the invention, the portion of SCR1 and SCR2 of CD55 comprises amino acids 83-93, 101-112 and 145-157 of the sequences shown in FIG. 1b.

The present invention further provides a screening method comprising the step of screening a library of candidate agents for the ability to inhibit the binding of a naked binding member to both SCR1 and SCR2 of CD55.

The assay of the invention may be a screen, whereby a number of candidate agents are tested. Accordingly, any suitable technique for screening compounds known to the person skilled in the art may be used. The screen may be a high-throughput screen. For example, WO84/03564 describes a method in which large numbers of peptides are synthesised on a solid substrate and reacted with an agent and washed. Bound entities are detected.

The invention also contemplates the use of competitive drug screening assays in which neutralising antibodies such as 791T/36 capable of binding SCR1 and 2 of CD55 specifically compete with a test compound for binding to SCR1 and 2 of CD55.

Agents identified by the screening method of the present invention and their use in the manufacture of a medicament for the treatment of cancer are also contemplated by the invention.

Preferred features of each aspect of the invention are as for each of the other aspects mutatis mutandis.

The invention will now be described further in the following non-limiting examples. Reference is made to the accompanying drawings in which:

FIG. 1a represents the translated CDR sequences of VK and VH cDNAs from 105AD7 hybridoma. Uppercase letters represent the CDR regions, the lower case letters are the adjacent framework amino acids. CDR1, CDR2, and CDR3 of VK correspond to amino acid residues 4-14 of SEQ ID NO: 1, 4-10 of SEQ ID NO: 3, and 4-12 of SEQ ID NO: 5, respectively. CDR1, CDR2, and CDR3 of VH correspond to amino acid residues 3-8 of SEQ ID NO: 2, 4-19 of SEQ ID NO: 4, and 4-19 of SEQ ID NO: 6, respectively.

FIG. 1b shows alignment of CDR peptides CDRL1, CDRH2, and CDRH3 from 105AD7 with amino acid residues 83-112 (SEQ ID NO: 7) and 138-161 (SEQ ID NO: 10) of CD55. The amino acid numbering is taken from the full-length sequence of CD55 including the leader sequence. CD55 peptides used in subsequent assays are shown underlined. Bullets (●) represent amino acid identity whereas amino acids with similar physicochemical properties are marked as (I).

FIG. 2 illustrates a C3b complement deposition assay. 791T cells were incubated with human serum as a source of complement. C3b deposition was measured using rabbit anti-C3b FITC labelled antibody in the presence of blocking (216), non blocking (220) or test antibody 791T/36. Fluorescence was quantified by a FACScan flow cytomemeter and is present as mean linear fluorescence (MLF).

EXAMPLE 1

CD55 Neutralisation Assay

Purified CD55 antigen was obtained by immunoaffinity-matrix purification from octyl-glucoside-solublised 791T cells. CD55 cDNA was cloned and sequenced using primers based on protein sequence data obtained from the purified antigen (Spendlove et al., 1999 Cancer Res 59, 2282). The DNA sequence obtained was identical to that identified by Caras et al and present on the Genbank database (Accession No. M31516).

Cells 791T is an osteosarcoma cell line which was grown in RPMI (Gibco, BRL, Paisley, and UK) supplemented with 10% heat inactivated fetal calf serum.

Monoclonal Antibodies

Monoclonal antibodies 791T/36 (IgG2b anti-791Tgp72; Embleton et al 1981 Br. J. Cancer 43:582-587), BRIC 216

(IgG1 anti-SCR 3 of CD55; Tate et al 1989 Biochem J 261, 489), BRIC 220 (IgG1 anti-SCR 1 of CD55, Tate et al 1989 Biochem J 261, 489), BRIC 110 (IgG1 anti-SCR 2 of CD55; Spring et al., 1987 Immunology 62 377; Coyne et al, 1992 J Immunol 149, 2906) have been reported previously. The BRIC antibodies were purchased from the Blood Group Reference laboratory (Bristol, UK).

Methods 791T tumour cells that over-express CD55 were washed with media containing 10% FCS and resuspended at a density of $1\times10^5$ cells per 100 µl. Primary antibody was incubated with 3× sample volume ($3\times10^5$ cells/300 µl) at a concentration of 50 µg/ml. Primary antibodies were positive control antibody, 216 (anti-SCR3), negative control antibody 220 (anti-SCR1) and test antibody, 791T/36 (anti-SCR1 and 2). Cells and antibodies were incubated for 1 hr at 4° C. prior to washing in PBS. Samples were split into 3 samples of 100 µl per tube. Human Serum was added as a source of complement to total concentration of 5% (Not Heat Inactivated). Tubes were inverted several times and incubate at 37° C. for 2 hours, mixing every 30 min. Cells were washed twice in PBS prior to addition of polyclonal rabbit anti human C3c FITC conjugated antibody (1/100) to a final volume of 100 µl. Cells were incubated for 1 hour at 4° C. prior to washing twice in PBS and resuspending in 200 µl of 1% cell fix.

Results

FIG. 2 shows that in the presence of a non-blocking antibody 220 C3b is deposited onto 791T cells at modest levels (MLF 200). In the presence of the CD55 neutralising antibody, 216, enhanced C3b deposition is observed (MLF 350). However in the presence of monoclonal antibody 791T/36 even greater levels of C3b are deposited (MLF520). This suggests that although 216 is an effective competitor with C3 convertase for binding to SCR3. binding of 791T/36 to SCR1 and SCR2 domains functionally inactivates CD55 leading to a 250% increase in C3b deposition.

EXAMPLE 2

Long Term Survival of Recurrent Colorectal Cancer Patients Receiving Radiolabelled 791T/36 for Tumour Imaging.

Antibody and Labelling

Hybridoma 791T/36 clone 3 is the source of antibody (791T/36, IgG2b isotype). Ascitic fluid from mice in which the hybridoma was developing was applied to a protein A-"Sepharose" column in pH 7.5 0.1 mol/l citrate phosphate buffer and the column was thoroughly washed. Bound immunoglobulins were eluted stepwise at pH 6.0, 5.0, 4.5 and 3.0 and these were then dialysed against phosphate-buffered saline. The dialysate was then centrifuged at 1000000 g for 1 h, filtered through a 0.22 µm Millex "Millipore" filter, and stored at −70° C. at a protein concentration of 1 mg/ml. The preparation contained only IgG2b as assessed by immunodiffusion tests with mouse immunoglobulin typing antisera (Miles Laboratories, Stoke Poges, Bucks.) and was pyrogen-free (Boots Pharmaceuticals, Notts).

Batches of the antibody preparation were labelled with $^{131}I$ by means of "Iodogen" reagent. Non-bound iodine was removed by gel filtration on sephadex G25. Labelled preparations were diluted into saline containing 1% serum albumin and sterilised by Millex filtration.

72 patients with recurrent colorectal cancer were imaged with the radiolabelled monoclonal antibody 791T/36. Patients received an id dose of 10 µg of antibody followed by an intravenous dose of 200 µg. 2dl of preparation containing 200 µg of antibody and approximately 70MBq $^{131}I$ was infused into an antecubital vein of each patient over 30 min.

Survival was followed for 7 years and compared to a contemporary group of recurrent colorectal cancer patients. There were 12 long term survivors (16%) in the patients who had received 791T/36 where as in contrast only 1 out of 89 patients survived 7 years in the contemporary group (p>0.001).

TABLE 1

Survival of colorectal cancer patients receiving 791T/36 antibody.

| Patients | Survival | Death |
|---|---|---|
| Imaged with 791T/36 | 12 | 60 |
| Contemporary controls | 1 | 88 |

These results suggest that there is an apparent survival benefit in a non-randomised trial of patients receiving radiolabelled 791T/36 antibody. The dose of radiolabel reaching the tumour is well below the level required to elicit tumour killing as a result of the radiolabel alone. It is therefore more likely that the antibody is inactivating CD55, allowing complement attack of residual tumour. As these patients only received a single intravenous dose of 791T/36 antibody the apparent survival benefit is very dramatic. Repeat injection with a humanised 791T/36 antibody may have an even more pronounced therapeutic benefit.

EXAMPLE 3

Production of New Monoclonal Antibodies to SCR1 and SCR2

6-8 week old Balb/c mice were immunised twice 3 weeks apart by intraperitoneal injection with 791T cells that over-express CD55 antigen ($10^6$ cells). Mice were then boosted with SCR1-2 protein fused to human Fc and purified by protein A chromatography. Mice were tail bled and serum was screened for their ability to recognise CD55SCR1-2/CD46SCR3-4 chimeric molecules expressed by CHO cells as previously described (Spendlove et al 2000 Eur J Immunol 30, 2944). They were also screened for their ability to recognise the SCR1-2CD55Fc protein and the IC, 2N and 2C peptides attached to BSA as previously described (Spendlove et al 2000 Eur J Immunol 30, 2944). Mice producing antibodies that recognises CD55SCR1 and SCR2 are boosted by an intravenous injection of SCR1-2Fc protein and splenocytes removed 5 days later and fused using PEG with NSO myeloma cells at a 10:1 ratio. Hybridomas are selected using HAT medium and screened for production of antibodies recognising SRR1-2Fc protein by ELISA. Hybridomas producing the correct antibody are cloned by limiting dilution three times a 1 cells per well to ensure clonality. The monoclonal antibody is screened for its ability to recognise CD55SCR1-2/CD46SCR3-4 chimaeric molecules expressed by CHO cells as previously described (Spendlove et al 2000 Eur J Immunol 30, 2944). They are also screened for their ability to recognise the SCR1-2CD55Fc protein and the IC, 2N and 2C peptides attached to BSA as previously described (Spendlove et al 2000 Eur J Immunol 30, 2944). To determine if they recognise the same site as 791T/36 plates are coated with CD55 as described above. They are then incubated with the new monoclonal antibodies and then with biotinylated 791T/36. Binding of 791T/36 is quantified by avidin peroxidase and ABTS substrate and the OD read at 405 nm on a plate reader. If the monoclonal antibodies recognise the same or related sites to 791T/36 they will inhibit binding of 791T/36 to CD55 antigen.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

REFERENCES

1. Liszewski, M. K., T. C. Farries, D. M. Lublin, I. A. Rooney, and J. P. Atkinson. 1996. *Adv Immunol* 61:201-283.
2. Hindmarsh, E. J., and R. M. Marks. 1998. *Eur J Immunol* 28:1052-1062.
3. Niehans, G. A., D. L. Cherwitz, N. A. Staley, D. J. Knapp, and A. P. Dalmasso. 1996. *Am J Pathol* 149:129-142.
4. Li, L., I. Spendlove, J. Morgan, and L. G. Durrant. 2001. *Br. J. Cancer* 84:80-86.
5. Thorsteinsson, L., G. M. O'Dowd, P. M. Harrington, and P. M. Johnson. 1998. *APMIS* 106:869-878.
6. Yamakawa, M., K. Yamada, T. Tsuge, H. Ohrui, T. Ogata, M. Dobashi, and Y. Imai. 1994. *Cancer* 73:2808-2817.
7. Bjorge, L., T. S. Jensen, and R. Matre. 1996. *Cancer Immunol Immunother* 42:185-192.
8. Simpson, K. L., A. Jones, S, Norman, and C. H. Holmes. 1997. *Am J Pathol* 151:1455-1467.
9. Juhl, H., F. Helmig, K. Baltzer, H. Kalthoff, D. Henne-Bruns, and B. Kremer. 1997. *J. Surgical Oncol.* 64:222-230.
10. Hindmarsh, E. J., and R. M. Marks. 1998. *J. Immunol.* 160:6128-6136.
11. Niehans, G. A., D. L. Cherwitz, N. A. Staley, D. J. Knapp, and A. P. Dalmasso. 1996. *Am. J. Pathol.* 149: 129-142.
12. Azuma, A., Y. Yamano, A. Yoshimura, T. Hibino, T. Nishida, H. Yagita, K. Okumura, T. Seya, R. Kannagi, M. Shibuya, and S. Kudoh. 1995. *Scand J Immunol* 42:202-208.
13. Blok, V. T., M. R. Daha, O. Tijsma, C. L. Harris, B. P. Morgan, G. J. Fleuren, and A. Gorter. 1998. *J Immunol* 160:3437-3443.
14. Harris, C. L., K. S. Kan, G. T. Stevenson, and B. P. Morgan. 1997. *Clin. Exp. Immunol.* 107:364-371.
15. Farrands, P. A., A. C. Perkins, M. V. Pimm, J. D. Hardy, M. J. Embleton, R. W. Baldwin, and J. D. Hardcastle. 1982. *Lancet* 2:397-400.
16. Farrands, P. A., A. Perkins, L. Sully, J. S. Hopkins, M. V. Pimm, R. W. Baldwin, and J. D. Hardcastle. 1983. *J. of Bone and Joint Surg.* 65:638-640.
17. Armitage, N. C., A. C. Perkins, M. V. Pimm, M. L. Wastie, and R. W. Baldwin. 1985 *Nucl Med Commun* 6:623-631.
18. Armitage, N. C., A. C. Perkins, M. V. Pimm, P. A. Farrands, R. W. Baldwin, and J. D. Hardcastle. 1984. *Br J Surg* 71:407-412.
19. Byers, V. S., M. V. Pimm, P. J. Scannon, I. Pawluczyk, and R. W. Baldwin. 1987. *Cancer Res* 47:5042-5046.
20. Byers, V. S., R. Rodvien, K. Grant, L. G: Durrant, K. H. Hudson, R. W. Baldwin, and P. J. Scannon. 1989. *Cancer Research* 49:6153-6160.
21. Spendlove, I., L. Li, J. Carmichael, and L. G. Durrant. 1999. *Cancer Res.* 59:2282-2286.
22. Embleton, M. J., B. Gunn, V. S. Byers, and R. W. Baldwin. 1981. *Br. J. Cancer* 43:582-587.
23. Loveland, B. E., M. Lanteri, P. Kyriakou, and D. Christiansen. 1998. *Molecular Immunology* 35:369 A155.
24. Lanteri, M., D. Christiansen, P. M. Hogarth, I. F. C. McKenzie, and B. E. Loveland. 1998. *Molecular Immunology* 35:369 A156.
25. Evans, M. J., S. L. Hartman, D. W. Wolff, S. A. Rollins, and S. P. Squinto. 1995 *J. Immunol. Methods* 184:123-138.
26. Casasnovas, J. M., M. Larvie, and T. Stehle. 1999. *The EMBO J.* 18:2911-2922.
27. Friedman, A. R., V. A. Roberts, and J. A. Tainer. 1994. *Proteins: Struct. Funct. Genet.* 20:15-24.
28. Stanfield, R. L., M. Takimoto-Kamimura, J. M. Rini, A. T. Profy, and I. A. Wilson. 1993. Structure 1:83-93.
29. Coyne K E, Hall S E, Thompson E S Arce M A, Inoshita T, Fujita T, Anstee D J, Rosse W, Lublin D M (1992). J Immunol 149 2906-2913.
30. Spring F A, Judson P A, Daniels S F, Parsons S F, Mallinson G and Anstee D J 91987). Immunology 62 377.
31. Tate C G, Uchikawa M, Tanner M J A, Judson P A, Parsons S F, Mallinson G and Anstee D J (1989). Biochem J 261, 489.
32. Gorter a, Blok V T, Haasnoot W H B, Ensink N G, Daha M R, Lauren G J (1996) Lab Invest 74 1039-1049.
33. Spendlove I, Li L, Potter V, Christiansen D, Loveland B and Durrant L G (2000) Eur J Immunol 30, 2944.

The invention claimed is:

1. A method of treating cancer comprising administration of a therapeutically effective amount of a naked antibody or fragment thereof which specifically binds to SCR1 and SCR2 of CD55 to a human in need thereof, wherein the cancer is colorectal cancer and wherein the colorectal cancer cells to be treated express CD55.

2. The method according to claim 1 wherein the antibody or fragment thereof binds to SCR1 amino acids 83-93 (corresponding to amino acid residues 1-11 of SEQ ID NO: 7), and SCR2 amino acids 101-112 and 145-157 (corresponding to amino acid residues 19-30 of SEQ ID NO: 7 and amino acid residues 8-20 of SEQ ID NO: 10, respectively).

3. The method according to claim 1 wherein the antibody or fragment thereof comprises the CDRs of the antibody produced by the cell line deposited at ATCC under accession number HB9173.

4. The method according to claim 1 wherein the antibody is the antibody 791T/36 produced by the hybridoma cell deposited at ATCC under accession number HB9173.

5. The method according to claim 1, further comprising co-administration of a therapeutically effective amount of an active agent with the therapeutically effective amount of the naked antibody or fragment thereof, wherein the active agent is selected from the group consisting of a chemotherapeutic agent, a pain relief agent, an antibody other than antibody 791T/36 and an anti-emetic.

6. The method according to claim 5, wherein the active agent is selected from the group consisting of doxorubicin, paclitaxel, 5-fluorouracil, irinotecan and cisplatin.

7. The method according to claim 5, wherein the active agent is an antibody other than antibody 791T/36.

8. The method according to claim 7, wherein the active agent is selected from the group consisting of an anti-CD20 antibody, an anti-VEGF antibody, an anti-CD171A antibody, an anti-CEA antibody, anti-idiotypic antibody, an anti-HMFG anti-diotypic antibody, an anti-EGFR antibody and an anti-HER2 antibody.

9. A method of treating cancer comprising administration of a therapeutically effective amount of a naked antibody or fragment thereof which specifically binds to SCR1 and SCR2 of CD55 to a human in need thereof, wherein the naked antibody is not antibody 791T/36, wherein the cancer is colorectal cancer, and wherein the colorectal cancer cells to be treated express CD55.

10. A method of treating cancer comprising co-administration of (1) a therapeutically effective amount of a naked antibody or fragment thereof which specifically binds to SCR1 and SCR2 of CD55, and (2) a therapeutically effective amount of an active agent, wherein the combination of naked antibody or fragment thereof and active agent are co-administered to a human and act synergistically by specifically enhancing complement deposition and complement-dependent lysis of cancer cells, wherein the cancer is colorectal cancer, and the colorectal cancer cells to be treated express CD55.

11. The method according to claim 10 wherein the naked antibody or fragment thereof binds to SCR1 amino acids 83-93 (corresponding to amino acid residues 1-11 of SEQ ID NO: 7), and SCR2 amino acids 101-112 and 145-157 (corresponding to amino acid residues 19-30 of SEQ ID NO: 7 and amino acid residues 8-20 of SEQ ID NO: 10, respectively).

12. The method according to claim 10 wherein the naked antibody or fragment thereof comprises the CDRs of the antibody produced by the cell line deposited at ATCC under accession number HB9173.

13. The method according to claim 10 wherein the naked antibody is the antibody 791T/36 produced by the hybridoma cell deposited at ATCC under accession number HB9173.

14. The method according to claim 10, wherein the active agent is an antibody selected from the group consisting of an anti-CD20 antibody, an anti-CD171A antibody, an anti-CEA antibody, and an anti-EGFR antibody, or a fragment thereof that comprises an antigen binding domain.

* * * * *

UNITED STATES PATENT AND TRADEMARK OFFICE
CERTIFICATE OF CORRECTION

| | |
|---|---|
| PATENT NO. | : 9,580,512 B2 |
| APPLICATION NO. | : 12/559342 |
| DATED | : February 28, 2017 |
| INVENTOR(S) | : Lindy Gillian Durrant |

It is certified that error appears in the above-identified patent and that said Letters Patent is hereby corrected as shown below:

In the Claims

Claim 8
Column 23, Lines 14 and 15, "anti-HMFG anti-diotypic antibody" should read --anti-HMFG anti-idiotypic antibody--.

Signed and Sealed this
Ninth Day of May, 2017

Michelle K. Lee
*Director of the United States Patent and Trademark Office*

SEQUENCE LISTING

```
<160> NUMBER OF SEQ ID NOS: 11

<210> SEQ ID NO 1
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 1

Ile Thr Cys Arg Ala Ser Gln Asp Ile Ser Ser Phe Leu Asn Trp Tyr
1               5                   10                  15
```

Gln

<210> SEQ ID NO 2
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 2

Asn Thr Ser Gly Val Cys Val Gly Trp Ile
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 3

Leu Ile Tyr Ala Ala Ser Ile Leu Gln Ser Gly Val Pro
1               5                   10

<210> SEQ ID NO 4
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 4

Trp Leu Ala His Ile Tyr Trp Asp Asp Lys Arg Tyr Ser Pro Ser
1               5                   10                  15

Leu Lys Ser Arg Ile Thr
            20

<210> SEQ ID NO 5
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 5

Tyr Tyr Cys Gln Gln Ser Tyr Lys Thr Pro Pro Ser Phe Gly Gln
1               5                   10                  15

<210> SEQ ID NO 6
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 6

Cys Ala Gln Val Leu Tyr Tyr Asp Phe Trp Ser Gly Tyr Leu Glu Tyr
1               5                   10                  15

Phe Ala Tyr Trp Gly Gln
            20

<210> SEQ ID NO 7
<211> LENGTH: 30
<212> TYPE: PRT
<213> ORGANISM: Artificial Sequence

```
<220> FEATURE:
<223> OTHER INFORMATION: Synthetic polypeptide

<400> SEQUENCE: 7

Lys Gly Ser Gln Trp Ser Asp Ile Glu Glu Phe Cys Asn Arg Ser Cys
1               5                   10                  15

Glu Val Pro Thr Arg Leu Asn Ser Ala Ser Leu Lys Gln Pro
            20                  25                  30

<210> SEQ ID NO 8
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 8

Arg Ala Ser Gln Asp Ile Ser Ser Phe Leu Asn
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 9

Trp Asp Asp Lys Arg Tyr Ser Pro Ser Leu Lys Ser
1               5                   10

<210> SEQ ID NO 10
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 10

Ser Leu Ser Pro Lys Leu Thr Cys Leu Gln Asn Leu Lys Trp Ser Thr
1               5                   10                  15

Ala Val Glu Phe Cys Lys Lys Lys
            20

<210> SEQ ID NO 11
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 11

Val Leu Tyr Tyr Asp Phe Trp Ser Gly Tyr Leu Glu Tyr
1               5                   10
```